United States Patent
Shinohara et al.

(10) Patent No.: US 6,188,744 B1
(45) Date of Patent: Feb. 13, 2001

(54) X-RAY CT APPARATUS

(75) Inventors: Hisahiro Shinohara, Tokyo; Masahiro Ozaki; Manabu Hiraoka, both of Tochigi, all of (JP)

(73) Assignee: Kabushiki Kaisha Toshiba, Kawasaki (JP)

(*) Notice: Under 35 U.S.C. 154(b), the term of this patent shall be extended for 0 days.

(21) Appl. No.: 09/280,725

(22) Filed: Mar. 30, 1999

(30) Foreign Application Priority Data

Mar. 30, 1998 (JP) .................................................. 10-084307

(51) Int. Cl.$^7$ ........................................................ A61B 6/03
(52) U.S. Cl. ................................................ 378/8; 378/901
(58) Field of Search ............................... 378/4, 8, 16, 901

(56) References Cited

U.S. PATENT DOCUMENTS

| | | | |
|---|---|---|---|
| 4,477,923 | 10/1984 | Baumann et al. | 378/95 |
| 5,459,769 | 10/1995 | Brown | 378/4 |
| 5,594,772 | 1/1997 | Toki et al. | 378/114 |
| 5,612,985 | * 3/1997 | Toki et al. | 378/4 |
| 5,687,208 | * 11/1997 | Bae et al. | 378/8 |
| 5,987,093 | * 11/1999 | Ozaki | 378/901 |

FOREIGN PATENT DOCUMENTS

| | | |
|---|---|---|
| 2624927 | 4/1997 | (JP) . |
| 10-127621 | 5/1998 | (JP) . |

* cited by examiner

*Primary Examiner*—David P. Porta
*Assistant Examiner*—Drew A. Dunn
(74) *Attorney, Agent, or Firm*—Oblon, Spivak, McClelland, Maier & Neustadt, P.C.

(57) ABSTRACT

A plurality of regions of interest can be set to be monitored. From a keyboard (17) or a mouse (19), ROI position information and CT value conditions for the ROI's are set to a ROI position information memory (39) and a ROI condition memory (21), respectively. An image reconstruction system (9) reconstructs data of a first scan stored in a projection data memory, displays as a reconstruct image (59) on a display device (13) via an image memory (11), and calculates individual representative CT values of the ROI's set as the ROI position information, storing in the image memory (11). A condition decision section (43) of a CPU (15) makes decisions of whether the representative CT values of the ROI's meet the conditions in the ROI condition memory (21), executes an operation between respective results of the decisions to decide whether the first scan is to be continued or shifted to a second scan.

10 Claims, 11 Drawing Sheets

FIG.7A
| NO | ORGANS | DISEASE-a |
|----|--------|-----------|
| 1  | LIVER  | CANCER    |
| 2  | HEART  | VALVULAR DISEASE |
| 3  | LUNGE  | CANCER    |
| 4  |        |           |
150
FIG.7B
| NO | RADIOGRAPHIC COND. | DISPLAY COND-1 |
|----|--------------------|----|
| 1a | INTERMITTENT SCAN (PARAMETERS) | PLURAL IMAGES (PARAMETERS) |
| 1b | SYNCHRONOUS SCAN (PARAMETERS) | GRAPHIC DISPLAY (PARAMETERS) |
160
FIG.8A
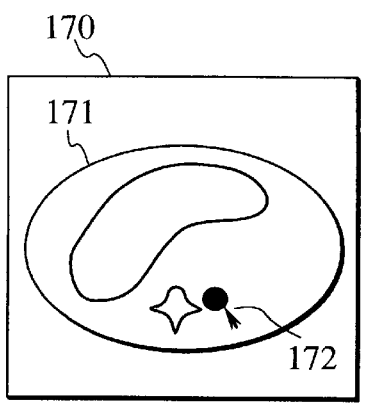
FIG.8B
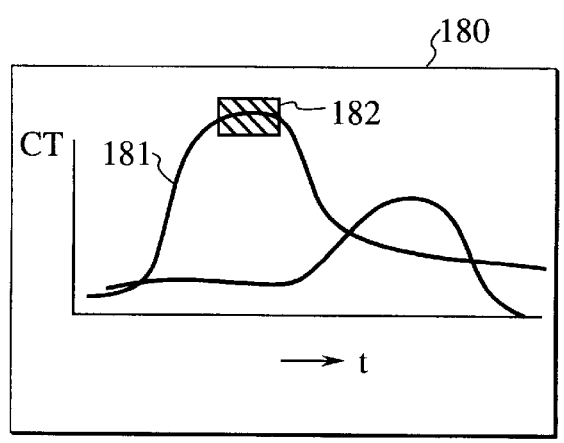

X-RAY CT APPARATUS

BACKGROUND OF THE INVENTION

1. Field of the Invention

The present invention relates to an X-ray CT (computer tomography) apparatus, and particularly, to an X-ray CT apparatus which has a real time CT value monitoring function, and is adapted to perform a monitoring of a CT value of a region of interest by a first scan and, when the CT value meets a predetermined condition, to execute a second scan for acquiring a clinical application image.

2. Description of Related Art

In a recent X-ray CT apparatus, with advancements for the detector to have higher performances and for the operational processor to have higher speeds, there has been achieved a real time reconstruction in which, while a scan is advancing, an image reconstruction is performed for display.

In a system, a technique for the real time reconstruction is applied to an X-ray CT radiography using contrast media, for monitoring a real time CT value. The system performs a first scan after injection of contrast media, monitoring a CT value of a region of interest, and performs a second scan when the state of distribution of the contrast media is optimized, acquiring an adequately media-contrasted image.

In the real time CT value monitoring system, a CT value of the region of interest is monitored in real time, and the image of an optimal state of distribution of contrast media is acquired in the second scan. Therefore, it is allowed for the contrast media to be decreased in quantity in use to reduce a burden on a patient, as well as for the number of scan times to be decreased to reduce the radiation exposure.

In an X-ray CT apparatus provided with such a system, a single region of interest is designated in a first scan and employed as an object of real time CT value monitoring.

Accordingly, the timing for a second scan to be executed is based on a decision on a CT value of the single region of interest, and the CT value needs to be always grasped at a high accuracy.

As a result, when subjected to a disturbance due such as to a movement of a patient, for example, the CT apparatus may have a different decision. As a countermeasure, the region of interest may be set at a point small of influences of such disturbances, or the apparatus is to cope with in a direction to discern a substance of the disturbance, having an exponentially increased quantity of computer resources allotted thereto, with an extended apprehension that the region of interest may be designated under restricted conditions.

SUMMARY OF THE INVENTION

The present invention has been achieved with such points in view. It therefore is an object of the invention to provide an X-ray CT apparatus in which a CT value of a region of interest to be monitored in a first scan does not need to be always grasped at a high accuracy, but can be grasped at a necessary accuracy, as circumstances require, to execute a second scan at an adequate timing.

To achieve the object, an aspect of the invention provides an X-ray CT apparatus adapted to perform a monitoring of a CT value of a region of interest by a first scan and, when the CT value meets a predetermined condition, to execute a second scan for acquiring a clinical application image, wherein the X-ray CT apparatus has region-of-interest setting means adapted for setting a plurality of regions of interest for the monitoring to be performed.

According to the aspect of the invention, a plurality of regions of interest can be set by the region-of-interest setting means, each as the region of interest for the monitoring to be performed of the CT value in the first scan.

BRIEF DESCRIPTION OF THE ACCOMPANYING DRAWINGS

The above and further objects and novel features of the present invention will more fully appear from the following detailed description when the same is read in conjunction with the accompanying drawings, in which:

FIGS. 7A and 7B are illustrations of exemplary tables stored in a condition memory of the X-ray CT apparatus of FIG. 6, in which FIG. 7A illustrates an examination object table, and FIG. 7B, a parameter table;

FIGS. 8A and 8B are illustrations of examples to be displayed on a monitor of the X-ray CT apparatus of FIG. 6, in which FIG. 8A illustrates an image window, and FIG. 8B, a CT value monitoring window;

FIGS. 10A and 10B are illustrations of exemplary monitor pictures in a single slice mode of the X-ray CT apparatus of FIG. 9, in which FIG. 10A illustrates an attribute emphasizing picture, and FIG. 10B, a time-differential picture;

FIGS. 11A and 11B are illustrations of exemplary monitor pictures in a multiple slice mode of the X-ray CT apparatus of FIG. 9, in which FIG. 11A illustrates a multiple slice picture, and FIG. 11B, a slice position displaying picture;

FIGS. 13A and 13B are illustrations of exemplary pictures to be displayed on a monitor of the X-ray CT apparatus of FIG. 12, in which FIG. 13A illustrates an entirety of a picture, and FIG. 13B, an example to be displayed as a reference image window;

FIGS. 14A and 14B are illustrations of exemplary pictures to be displayed on a monitor of the X-ray CT apparatus of FIG. 12, in which FIG. 14A illustrates a normal example of a CT value monitoring window, and FIG. 14B, a corresponding example to be displayed as a reference image window;

FIGS. 15A and 15B are illustrations of exemplary pictures to be displayed on a monitor of the X-ray CT apparatus of FIG. 12, in which FIG. 15A illustrates an example of a CT value monitoring window displaying an abnormal CT value, and FIG. 15B, a corresponding example to be displayed as a reference image window.

DETAILED DESCRIPTION OF THE PREFERRED EMBODIMENTS

Figure 1:
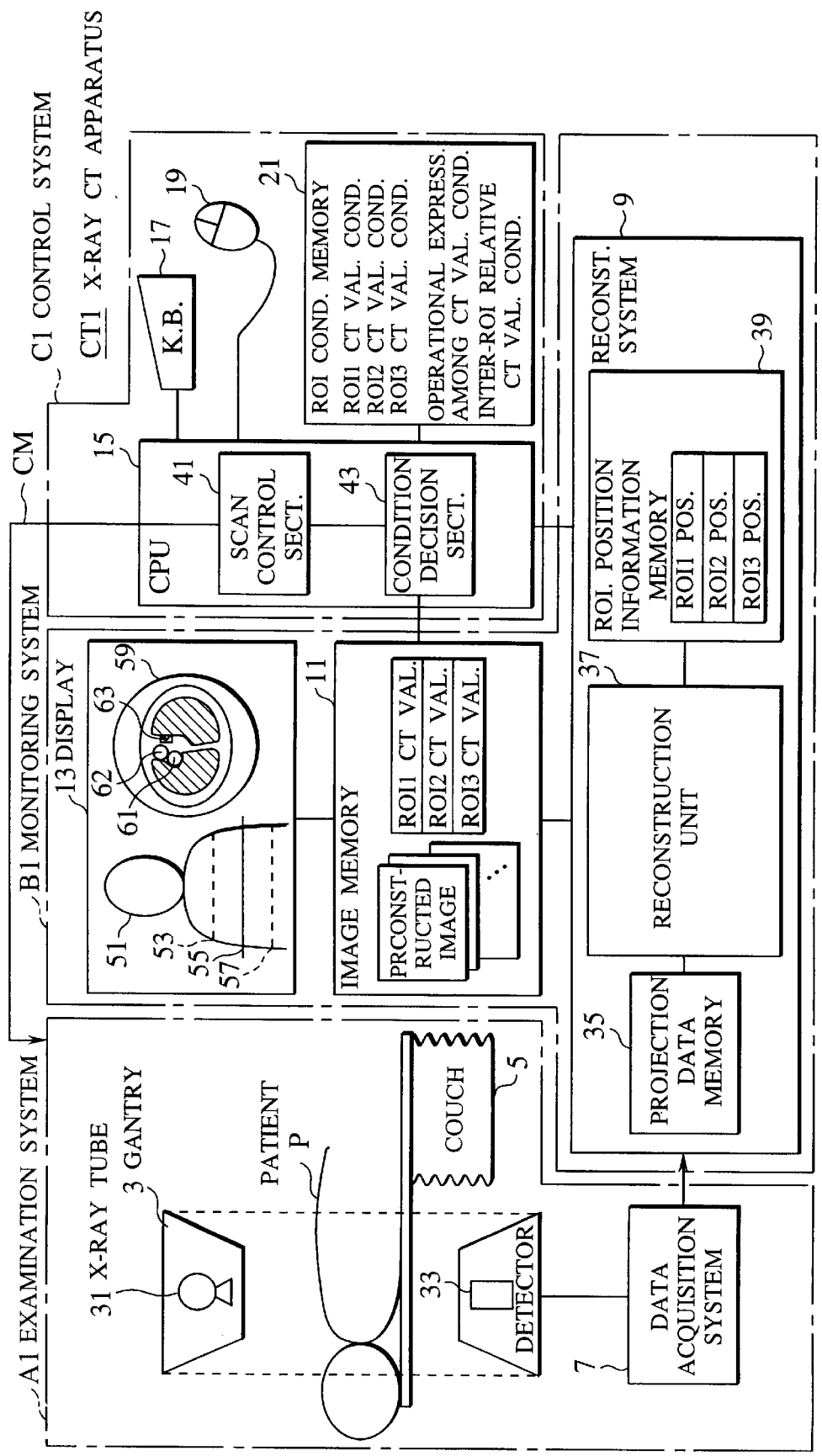
FIG. 1 is a block diagram of an X-ray CT apparatus according to a first embodiment of the invention.

There will be detailed below the preferred embodiments of the present invention with reference to the accompanying drawings, in which elements having like functions are designated by like reference characters to avoid redundant description.

Firstly, there will be described a first embodiment of the invention with reference to FIGS. 1 to 5.

As shown in FIG. 1, an X-ray CT apparatus CT1 comprises: an examination system A1 for scanning a patient P in one of a plurality of X-ray scan modes to sample scan data; a monitoring system B1 responsible for scan data sampled by the examination system A1 to reconstruct and display a monitoring image of a scanned portion of the patient P, and for processing CT data of respective regions of interest (hereafter sometimes each called "ROI") set up in a displayed image in a later-described manner, to provide value data (hereafter sometimes each called "representative CT value" or simply "CT value") representative of them by regions; and a control system C1 for recognizing a comprehensive nature of the value data consisting of a plurality of CT values in light of a relationship with a portion of the patient P to be examined, to provide a control command CM to the examination system A1 based on a result of the recognition. The comprehensive nature of the value data to be recognized by the control system C1 (i.e. an attribute) and the conspicuousness (i.e. its significancy) are defined by a variety of conditions set in a later-described manner. While the examination system A1 is in a scan mode for a first scan, if the set conditions are met, then the control command CM includes a start signal for a second scan.

The examination system A1 comprises a rotary scan gantry 3 including an X-ray tube 31 serving as an X-ray source and a dose detector 33; a couch device 5 including a top plate for placing thereon the patient P to be displaced in the longitudinal direction of the patient P; and a projection data acquisition system (DAS) 7 for amplifying and A/D-converting detection signals of the detector 33, collecting resultant projection data. The dose detector 33 comprises a detector array, which is constituted by a plurality of detectors arranged in an arc shape to have a focal point of the X-ray tube as the center, and detects X-rays transmitted through the patient to be examined in multiple channels.

The monitoring system B1 comprises: a reconstruction system 9 including a memory 35 for storing projection data, a reconstruction unit 37 for reconstructing a scanogram or a tomographic image based on projection data read from the memory 35 and calculating representative CT values of regions of interest, and a ROT position information memory 39 for storing coordinate data of the regions of interest, as they are set; an image memory 11 for storing the scanogram or the tomographic image and the CT values of the regions of interest which are plural in number; and a display device 13 for displaying the image stored in the image memory 11 to thereby function as an output device to an operator.

Thee control system C1 comprises: a console including a CPU(central processing unit) for controlling an entirety of the X-ray CT apparatus CT1; an input device including a keyboard 17 and a mouse 19 and adapted for inputting positions and configurations of a plurality of regions of interest, individual CT value conditions for the regions of interest, an operational expression between the CT value conditions, and other necessary matters; and a ROI condition memory 21 for storing set conditions, such as the individual CT value conditions for the regions of interest, the operational expression between the CT value conditions.

Note that the display device 13 of the monitoring system B1 is disposed at a display section of the console, and is interactive with an operator of the console through its display screen and the input device of the control system C1.

In the gantry 3, the X-ray tube 31 and the detector 33, disposed in opposition to each other, are driven by a rotary drive mechanism to rotate about a longitudinal axis of the patient P, thereby examining an intensity distribution of an X-ray projection about the patient P.

In the reconstruction system 9, the projection data memory 35 stores therein projection data transmitted from the data acquisition system 7, the ROI position information memory 39 stores therein positions and configurations of a plurality of regions of interest, as they are input through the input device including the keyboard 17 and the mouse 19, and the reconstruction unit 37 employs data of the projection data memory 35 to reconstruct a tomographic image and calculates representative CT values of the regions of interest stored in the ROI position information memory 39.

The CPU 15 is provided with a scan control section 41 and a condition decision section 43, and constitutes a substantial body of the console controlling the entirety of the X-ray CT apparatus CT1. The scan control section 41 is adapted, via the control command CM, to have the rotary drive mechanism rotate the X-ray tube 31 and the detector 33 of the gantry 3 and concurrently control a high voltage power supply for supplying high voltage to the X-ray tube 31 and the couch device 5, thereby coping with a plurality of scan modes including a scanoscopy of the patient P, a reference image acquiring scan, a first scan for a monitoring, and a second scan which may be called an actual scan or a subsequent scan in a case.

The first scan is a scan for monitoring CT values of regions of interest, and the monitoring is implemented to determine a timing for the second scan to be executed. Therefore, in usual, the first scan is performed with low X-ray dose, and continuously or intermittently after injection of contrast medium. To this point, the second scan is a scan to acquire a CT image possibly multivalent and the more effective for purposes of clinical applications, and needs considerations, such as for a start to be triggered just before a contrast medium distribution enters an optimum state for example, to pick up as much information as possible from an examination object, so that the X-ray dose also is relatively high.

In some cases, the first scan may be executed as a pilot scan accompanying no longitudinal relative movements between the gantry 3 and the patient P. In such a case, the detector 33 may be a single slice detector, and acquire a single tomographic image. In a certain system, there may be given multiple slices of tomographic images, as the detector 33 may comprise a multiple slice detector and the X-ray tube 31 may project a conical beam corresponding to the detector.

The condition decision section 43 of the CPU 15 reads respective representative CT values of plural regions of interest, as they are calculated in the reconstruction system 9 and stored in the image memory 11, and respective CT value conditions of the regions of interest, as they are stored in the ROI condition memory 21, to decide whether or not the former meets the latter. It reads also an operational expression between the CT value conditions of the regions of interest, if this is stored, and executes an operation; and makes a decision to permit a shift from the first scan to the second scan, when all the conditions are met.

There will be described how to set regions of interest and conditions for a decision, with reference to FIGS. 2 and 3.

Figure 2:
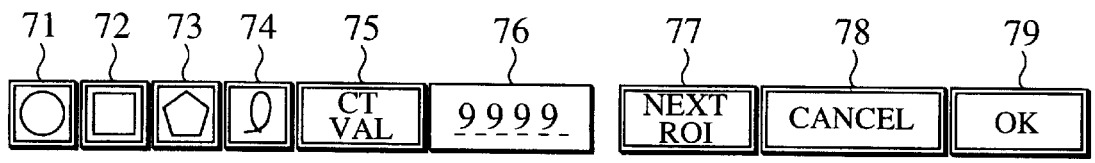
FIG. 2 is an illustration of exemplary icons to be displayed for setting regions of interest and CT value conditions in the X-ray CT apparatus of FIG. 1.

FIG. 2 illustrates setup icons 71 to 79 displayed on a screen of the display device 13. The icons 71 to 79 are employable for setting a combination of positions and configurations of plural regions of interest, and for setting individual threshold values for significancy decisions on respective representative CT values of the regions of interest. The icons may be constituted as panel switches of the console. This embodiment provides for the number of settable regions of interest to be three, for convenient description, which may however be four or more.

Figure 3:
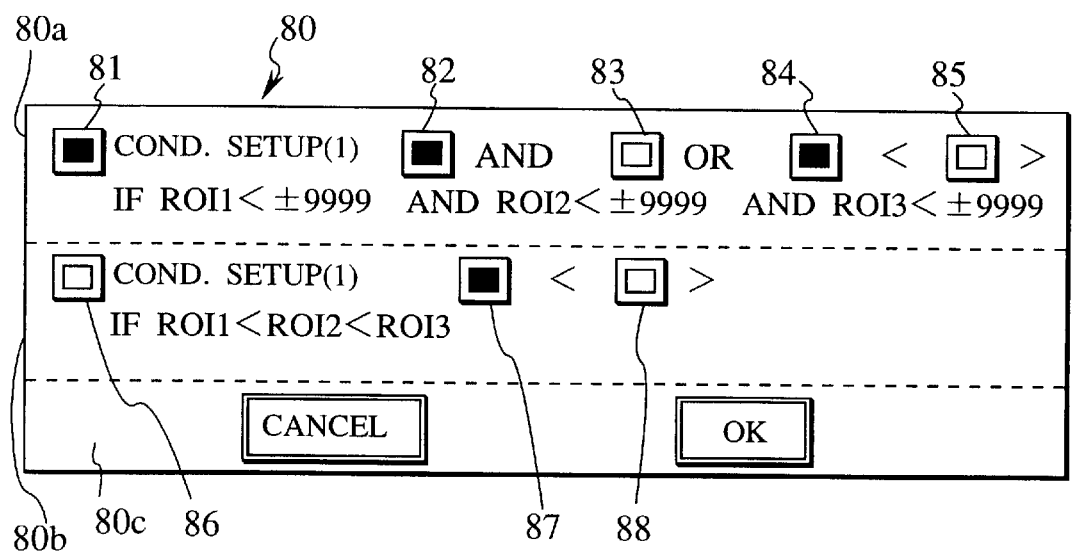
FIG. 3 is an illustration of exemplary windows to be displayed for setting CT value conditions between the regions of interest and operational expressions in the X-ray CT apparatus of FIG. 1.

FIG. 3 illustrates a condition setting window 80 displayed on the screen of the display device 13. The window 80 has an upper region 80a labeled "COND. SETUP (1)", an intermediate region 80b labeled "COND. SETUP (2)", and a lower region 80c. The COND. SETUP (1) region 80a is employable for setting individual comparative conditions (inequalities) between threshold values and representative CT values of respective regions of interest set by the icon 76, and for setting an operational expression defining a logical condition (AND/OR) for a comprehensive decision to be made, over all the regions of interest, on results of individual decisions made by the conditions for the regions of interest. Incidentally, the threshold values, the comparative conditions, and combinations thereof are each assumed as a CT value condition.

The COND. SETUP (2) region 80b is employable for setting a condition (a combination of inequalities) for a comprehensive comparison of representative CT values of a plurality of regions of interest. The comparative condition in this case also is assumed as a CT value condition.

The icons 71 to 74 are selectively employable for setting a number of regions of interest of voluntary configurations at voluntary locations on a tomographic image 59 (FIG. 1). When setting a circular region of interest, the icon 71 of a ○ mark is selective, and when setting a rectangular region of interest, the icon 72 of a □ mark. The icon 73 is selective for setting a region of interest of a polygonal form, and the icon 74, for setting a region of interest of a voluntary configuration.

In use of the icons 71 to 73, any of them can be selected and handled, e.g. by the mouse 19, to thereby set a region of interest of a corresponding configuration at a voluntary location on the tomographic image 59. Dimensions of the set region of interest can also be changed, and can be expanded or contracted in a voluntary manner by dragging part of a boundary line of a circumference of the region.

In use of the icon 74, loci of a cursor associated with motions of the mouse 19 are employed to describe a closed curve on the image, enclosing a region of a voluntary configuration to be set as a region of interest. Any region of interest set up through the input device, e.g. via the keyboard 17 or the mouse 19, is stored in the ROI position information memory 39 by the CPU 15 and concurrently presented (at 61) on the tomographic image 59.

For a respective region of interest, as it has been set in position and configuration, the icon 75 of [CT VAL.] is selective in turn to thereby input a CT value condition for the region of interest.

When the icon 75 is selected, the icon 76 automatically displays thereon an average CT value of a region of interest that has been set just before.

Then, the keyboard 17 can be used for inputting therefrom a numeric value of four digits to be overwritten on the average CT value, or the keyboard and/or the mouse 19 can be used for incrementing or decrementing the average CT value, to thereby appropriately change a displayed value on the icon 76 to be set as a CT value condition with which a representative CT value of the corresponding region of interest is to be compared.

Then, the icon 77 of [NEXT ROI] is selective to enter a setting mode for a subsequent region of interest, where a position and a configuration of this region of interest is to be set in the described manner. As such, a setting is to be sequentially repeated of a region of interest as well as of an individual CT value condition for the region.

After setup operations of respective positions, configurations and CT value conditions for a necessary number of regions of interest 61, 62, 63, the icon 79 of [OK] is selective to fix the setting. To change a setting, as necessary, the icon 78 of [CANCEL] is employable for a re-setting from a first region of interest.

Next, for a comprehensive decision over CT values of a plurality of regions of interest, a logical operational expression is to be set. In FIG. 3, a rectangular icon 81 is selective to choose the COND. SETUP (1) region 80a, and an icon 86, to choose the COND. SETUP (2) region 80b.

In the COND. SETUP (1), an icon 84 or an icon 85 is selective to choose a sign of inequality (<, >) as a condition for comparison between a representative CT value of a respective region of interest and a CT value condition (threshold value) therefor, thereby defining a logical variable to be a truth ("1") when the condition is met, or a falsity ("0") when it is not met, and besides an icon 82 or an icon 83 is selective to designate a logical product (a combination of AND's) or a logical sum (a combination of OR's) between the logical variables, thereby setting a logical function F for the decision. The logical function F may be such that:

$$F=(ROI1>ct1)*(ROI2>ct2)*(ROI3>ct3) \qquad (1),$$

where ROIi ($1 \leq i \leq 3$) is a representative CT value of an i-th region of interest, as it is given by a first scan, cti ($1 \leq i \leq 3$) is a CT value condition (threshold value) for the i-th region of interest Symbol "*" denotes a logical product.

When ROI1 is greater than ct1, ROI2 is greater than ct2, and ROI3 is greater than ct3, then the logical function F of expression (1) is true, or otherwise, it is false.

The logical function F may be such that:

$$F=(ROI1>ct1)+(ROI2>ct2)+(ROI3>ct3) \qquad (2),$$

where ROIi ($1 \leq i \leq 3$) is a representative CT value of an i-th region of interest, as it is given by a first scan, and cti ($1 \leq i \leq 3$) is a CT value condition (threshold value) for the i-th region of interest. Symbol "+" denotes a logical sum.

The logical function F of expression (2) is true if any of conditions that ROI1 is greater than ct1, that ROI2 is greater than ct2, and that ROI3 is greater than ct3 is met, or false if and only when none of them is met.

As will be described later (at step S33), the truth value of the logical function F constitutes a base for a decision of whether a first scan is to be kept or to be shifted to a second scan.

In the COND. SETUP (2), an icon 87 or 88 is selective for setting, as a combination G of inequalities, a comprehensive comparative condition (i.e. large-small relationships) between representative CT values of a plurality of regions of interest. The inequality combination G may be such that:

$$G = ROI1 < ROI2 < ROI3 \quad (3)$$

where ROIi ($1 \leq i \leq 3$) is a representative CT value of an i-th region of interest based on projection data collected by a first scan.

Contents of setup operations at the COND. SETUP (1) or the COND. SETUP (2) can be fixed or canceled by an icon in the lower region 80c of the window 80.

Figure 4:
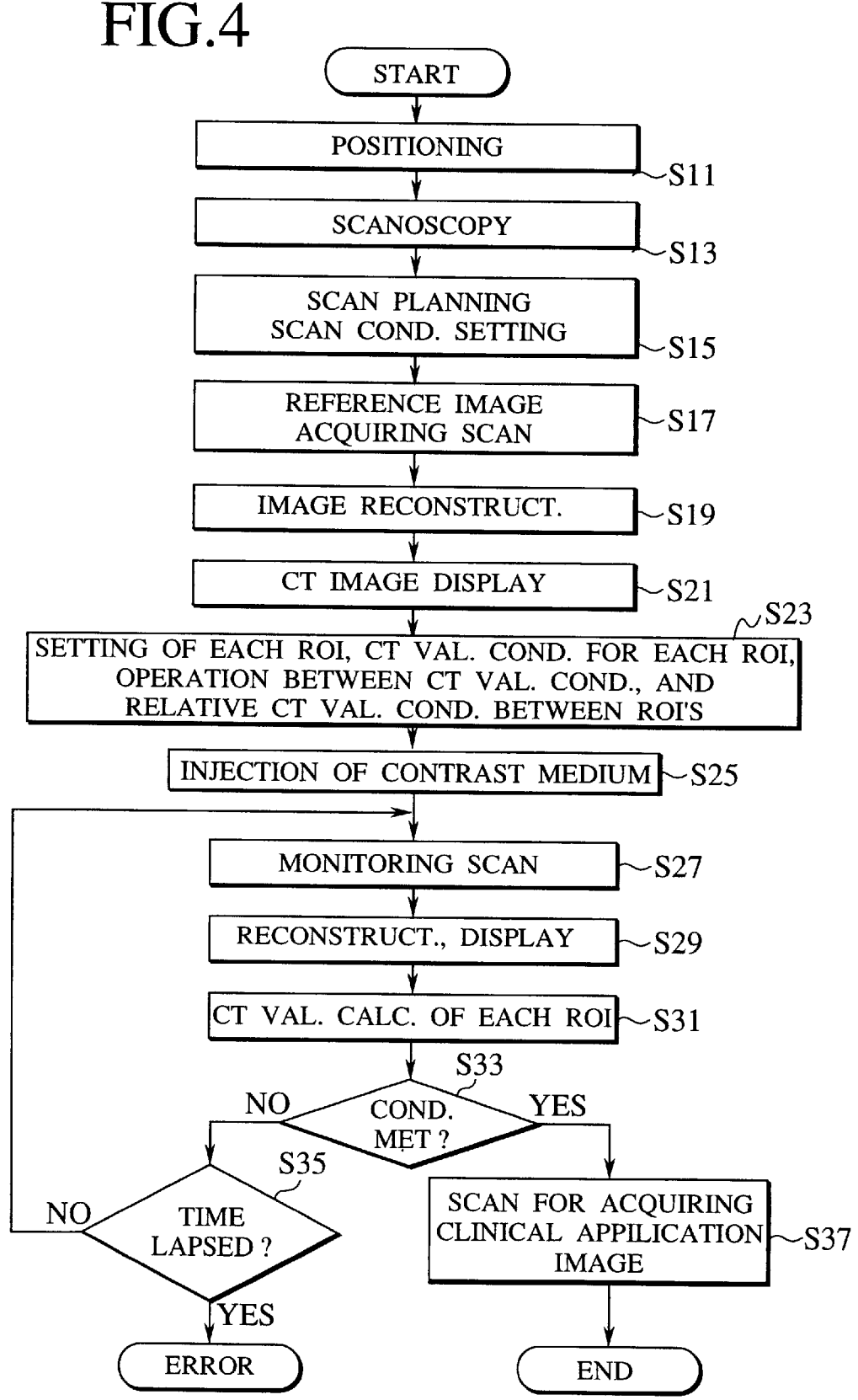
FIG. 4 is a flowchart describing functions of the X-ray CT apparatus of FIG. 1.

FIG. 4 is a flow chart describing functions of a real-time CT value monitoring system of the X-ray CT apparatus CT1 shown in FIG. 1.

First, a patient P is placed in position on the couch device 5 (at a step S11), the X-ray tube 31 is fixed to an upper portion of the gantry 3, and the patient P is displaced in a longitudinal direction, as a scanoscopic operation proceeds (at a step S13). A scanogram 51 (FIG. 1) obtained by the scanoscopic operation is displayed on the display device 13.

Next, with reference to the scanogram 51, a scan plan is prepared for a first-scan-oriented reference image acquiring scan, a first scan and a second scan. Then, associated settings are performed, such as of a slice position 55, a slice thickness, a scan start position 53, a scan end position 57, a tube voltage, and a tube current (at a step S15).

Next, the reference image acquiring scan is performed (at a step S17), a data reconstruction is effected by the reconstruction unit 37 (at a step S19), and a tomographic image 59 by the reference image acquiring scan is displayed on the display device 13 (at a step S21).

Next, with reference to the scanogram 51 and the tomographic image 59, a plurality of regions of interest are set on the tomographic image 59, and individual CT value conditions for the regions of interest as well as a logical operational expression between the individual CT value conditions for the regions of interest are set. A relative CT value condition between a plurality of regions of interest may be set, as necessary (at a step S23).

After the settings at the step S23 and a storing to the ROI condition memory 21, an injection of contrast medium is performed to the patient P in accordance with a body portion to be contrasted (at a step S25), a monitoring scan is entered (at a step S27), and the reconstruction system 9 performs an image reconstruction of a tomographic image and updates the displayed tomographic image 59 on the display device 13 (at a step S29).

Next, ROI positions and configurations stored in the ROI position information memory 39 are referred to by the reconstruction system 37, and a representative CT value of each region of interest is calculated, and stored in the image memory 11 (at a step S31).

As the representative CT value there usually is adopted an average value of all pixels in a region of interest, it may however be a median in a distribution of CT data values in the region of interest. For some applications, there may be employed a maximum value, a minimum value or an extreme value in the region of interest.

Next, a decision is made of whether or not a logical function defining an operation between CT value conditions for the regions of interest or a relative CT value condition between the regions of interest is met (at a step S33). If the condition is met, there is executed a scan for acquiring a clinical application image as the second scan (at a step S37), before the flow goes to an end.

After the decision at the step S33, unless the condition is met, another decision is made of whether or not a predetermined interval of time has elapsed from a start of the monitoring scan or the injection of contrast medium (at a step S35), and unless the predetermined time interval has elapsed, the flow branches to the step S27 for the monitoring of CT values of the regions of interest to be repeated. If the predetermined time interval has elapsed, there is given a judgment of time-out, an error is reported, and an adequate countermeasure thereto is taken.

The decision on a lapse of the predetermined time at the step S35 is for preventing an inefficient repetition of the monitoring scan due such as to a non-conformity in injection of contrast medium or setup of a CT value condition.

As such, CT values of a plurality of regions of interest are monitored through a first scan, and a decision is made for a shift from the first scan to a second scan on the basis of respective decisions on conditions as to whether or not representative CT values of the regions of interest individually meet CT conditions therefor, and a result of an operation between the decisions on the conditions, or by a relative CT value condition between the plurality of regions of interest, thus allowing for a flexible judgment of CT value condition to thereby detect an accurate distribution of contract medium, enabling a scanning at a timing with an optimal contract medium distribution.

For the conditional judgment of whether a representative CT value of a respective region of interest meets a CT value condition therefor, or as a relative CT value condition between a plurality of regions of interest, there may be employed not simply a large-small comparison but also a fuzzy logic.

Figure 5:
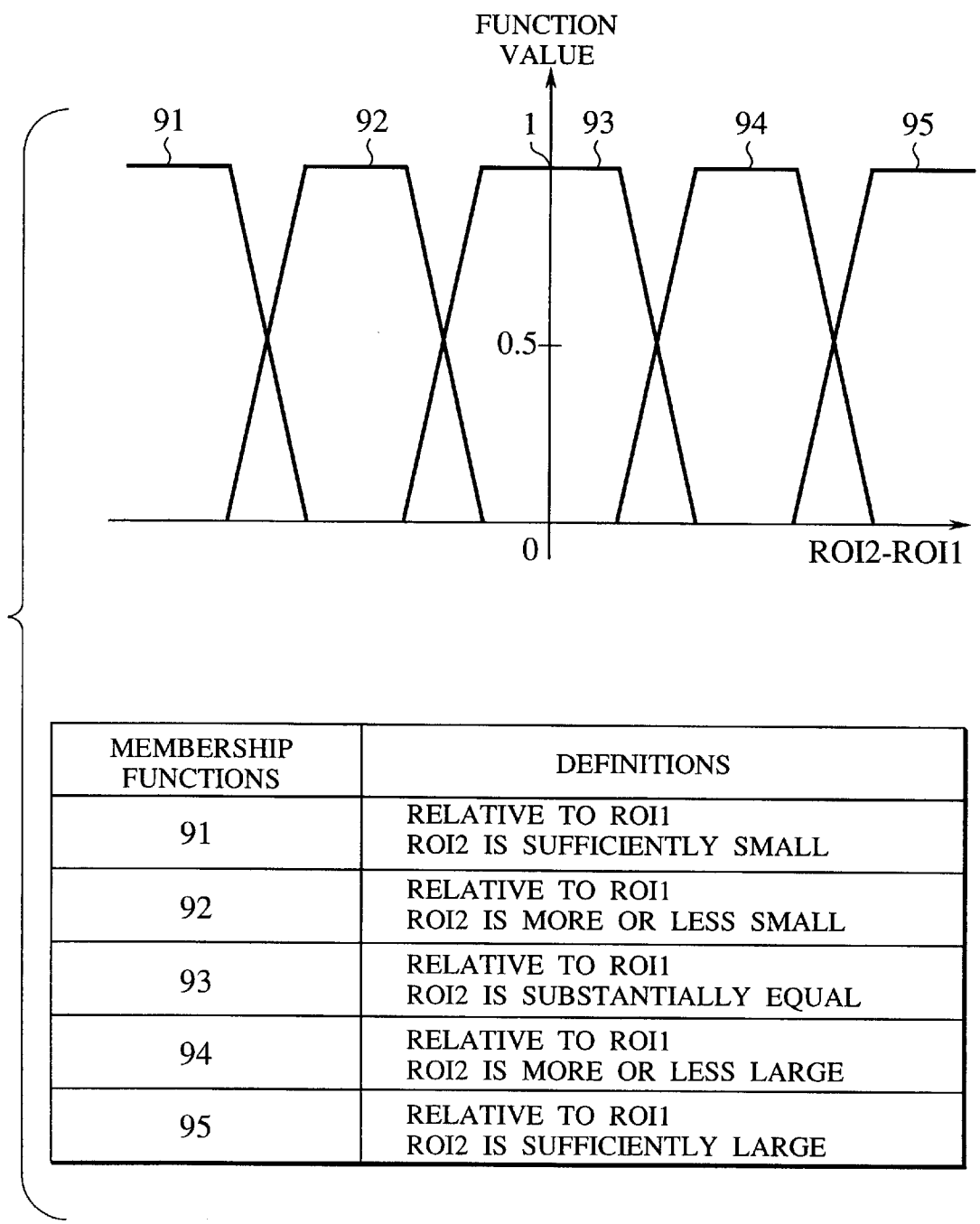
FIG. 5 is a graphic illustration of membership functions of a fuzzy logic applied to a decision by comparison of CT values between regions of interest in the X-ray CT apparatus of FIG. 1.

FIG. 5 illustrates membership functions 91 to 95 of a fuzzy logic applied to a comparison between a representative CT value (ROI1) of a first region of interest and a representative CT value (ROI2) of a second region of interest.

In the embodiment described, the number of regions of interest may be two or more, and a voluntary logic can be set as the logical operational expression between CT value conditions for a plurality of regions of interest.

The present embodiment is applicable to both a single slice X-ray CT apparatus and a multiple slice X-ray CT apparatus. In the latter case, multiple slices of tomographic images may have a plurality of regions of interest dispersed to be set therein as objects of a CT value monitoring.

The present embodiment has a plurality of regions of interest set for monitoring their CT values, without the conventional need of a very high accuracy to be always kept for a grasp of a single region of interest, resulting in a reduced restriction on the ROI setting.

The present embodiment is adaptive, against disturbances such as a movement of a patient in a first scan, for performing an accurate conditional decision on a representative CT value of each region of interest to monitor CT values of a plurality of regions of interest, executing various operations between the CT values, thereby achieving a flexible decision on a contrast state, allowing for a smaller injection quantity of contrast medium to acquire an image with an optimal contrast medium distribution.

Figure 6:
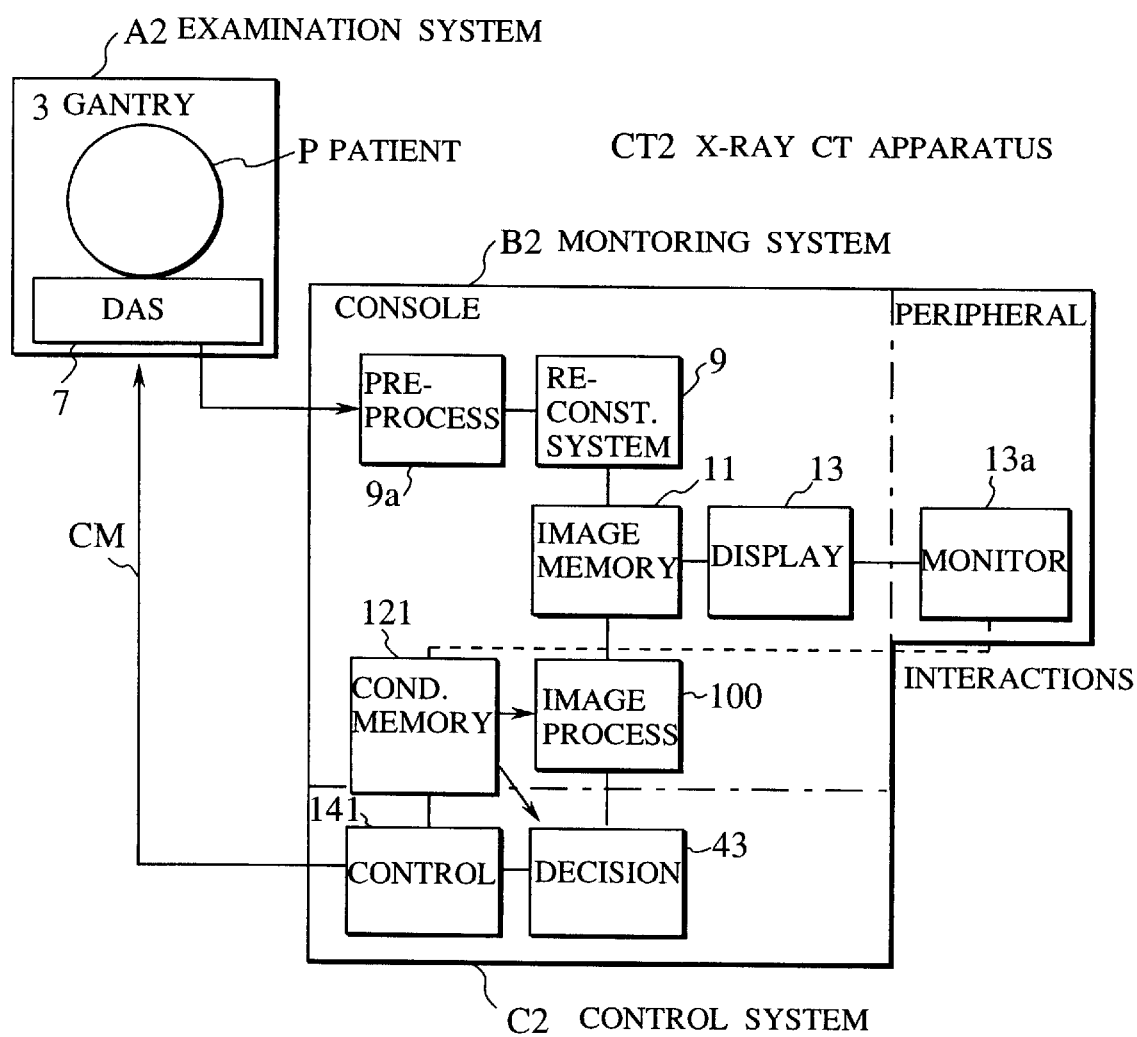
FIG. 6 is a block diagram of an X-ray CT apparatus according to a second embodiment of the invention.

Next, there will be described an X-ray CT apparatus CT2 according to a second embodiment of the invention, with reference to FIGS. 6, 7A, 7B, 8A and 8B. FIG. 6 shows the X-ray CT apparatus CT2 in a block diagram.

The X-ray CT apparatus CT2 according to the second embodiment comprises, like the first embodiment, an examination system A2 for sampling scan data, a monitoring system B2 for reconstructing a monitoring image and computing CT values of set regions of interest, and a control system C2 for recognizing a significant attribute of the CT values in light of set conditions to provide a control command CM, and has constitution and functions additionally described hereunder. A reconstruction system 9 of the monitoring system B2 is provided with a pre-process section 9a of projection data, and a display device 13 has an interactive monitor 13a as a peripheral.

The X-ray CT apparatus CT2 is constituted such that tables having varieties of preset monitoring conditions are stored via a control section 141 in a condition memory 121, and contents of the tables can be read out to an image processing device 100, a decision section 43 and the control section 141, as necessary, to be adequately set up or processed.

FIGS. 7A and 7B illustrate exemplary tables stored in the condition memory 121, in which FIG. 7A is an examination object table 150, and FIG. 7B, a parameter table 160 in a lower layer than the examination object table 150.

The examination object table 150 is a table which lists varieties of contrastive examination objects such as by organs and disease and which is displayed on the monitor 13a, allowing for one or more items (e.g. liver and cancer) in the displayed table 150 to be selected to thereby display on the monitor 13a the parameter table 160 as a listing of sets of corresponding or common parameters selected therefor.

Respective sets of parameters are categorized to be displayed such as by radiographic conditions, display conditions and trigger conditions, for example. For the graphic conditions, categories are sub-divided, such as by an intermittent scan and a synchronous scan, and additionally itemized in accordance with low dose mode, locations, etc. For the display conditions, there are displayed categories such as for plural images and graphic presentations, as well as names of images employable for a triggering or the like. For example, a certain name of image is selective to display an image window 170 showing an exemplary CT image 171, as illustrated in FIG. 8A. In the case of trigger conditions, there are given parametric presentations such as CT value, CT change ratio, ROI number, computed CT value range and ROI region, and a certain parameter, e.g. of the CT value, is selective to display a CT value monitoring window 180 showing CT curves 181, as illustrated in FIG. 8B, or the selection may be of the ROI region to provide a ROI presentation 172 and a representative CT value presentation 182, as illustrated in FIGS. 8A and 8B.

Further, there can be given a typical guiding presentation. For example, upon selection of a condition for a timing to be taken in artery phase for a liver cancer, associated conditions are set with a guiding presentation on where and how the contrast medium contrasts at the timing to be picked up.

Such conditions can be incorporated in a scan plan.

According to the present embodiment, it is unnecessary for complicate trigger conditions to be set up every examination, with a saved time and without apprehensions of an erroneous operation at a setting.

Figure 9:
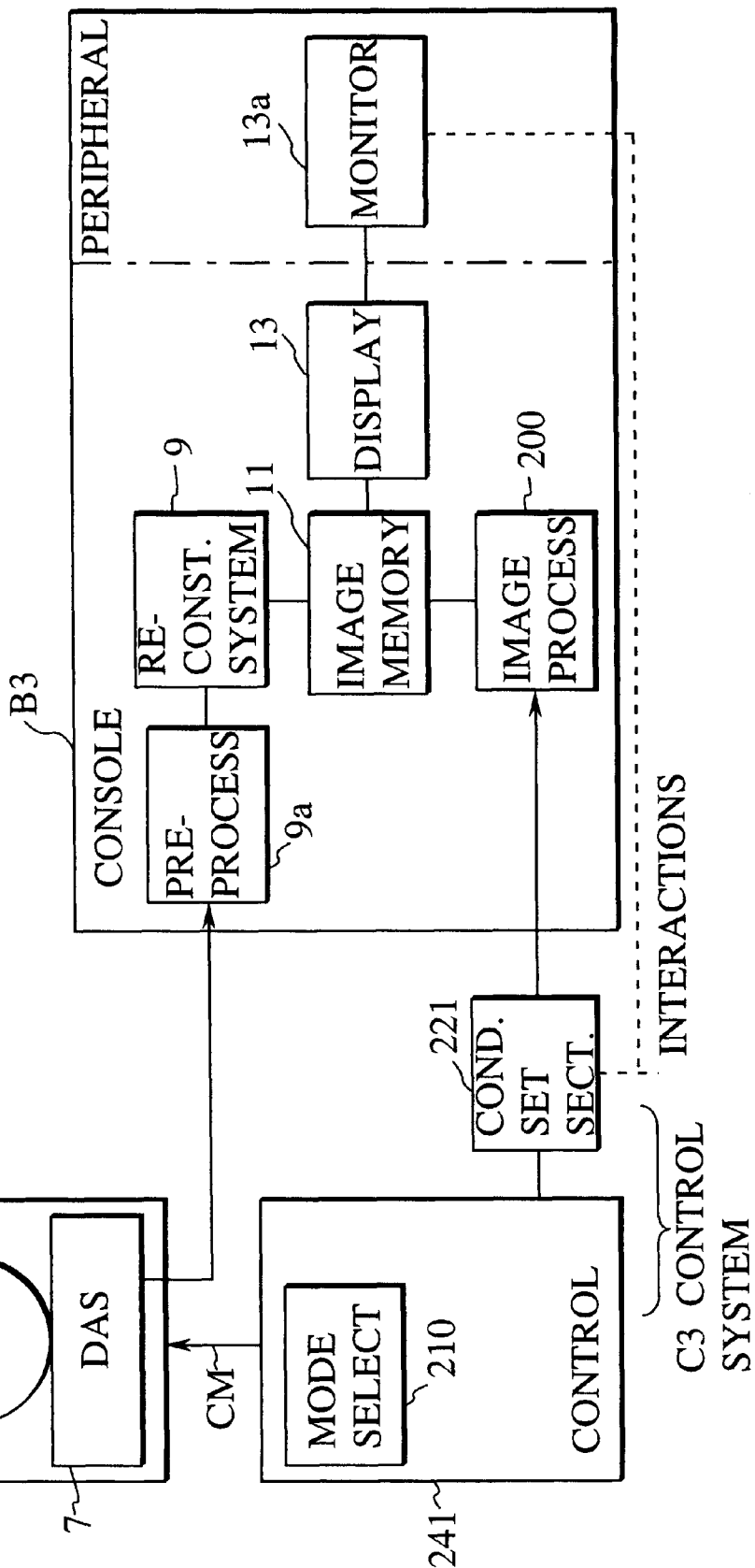
FIG. 9 is a block diagram of an X-ray CT apparatus according to a third embodiment of the invention.

Next, there will be described an X-ray CT apparatus CT3 according to a third embodiment of the invention, with reference to FIGS. 6, 10A, 10B, 11A and 11B. FIG. 9 shows the X-ray CT apparatus CT3 in a block diagram.

The X-ray CT apparatus CT3 according to the third embodiment comprises an examination system A3, a monitoring system B3 and a control system C3 each having like functions to the second embodiment, and has constitution and functions additionally described hereunder.

In this embodiment, the control system C3 has a section 210 for mode selection between a single slice mode and a multiple slice mode, and a condition setting section 221 has a preset table of data corresponding to functions described below, allowing for selected data to be processed at an image processing device 200 to have a plurality of images concurrently displayed on a monitor 13a.

Figure 10A:
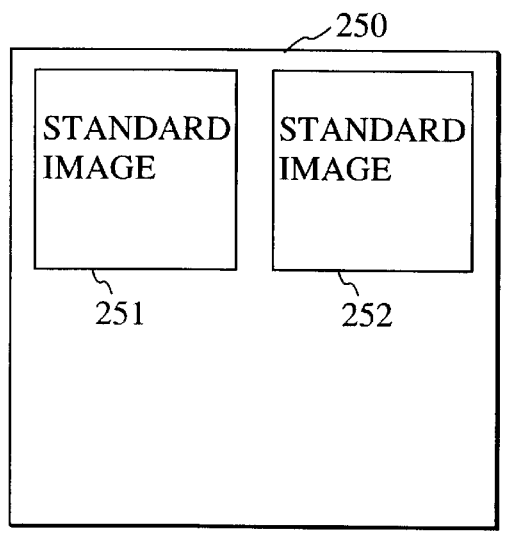
Figure 10B:
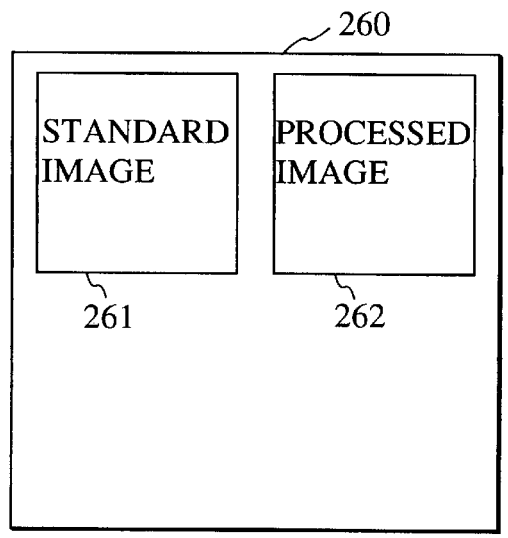

FIGS. 10A and 10B illustrate exemplary monitor pictures to be displayed on the monitor 13a in the single slice mode in which a slice thickness can be changed in a short time. FIG. 10A illustrates a picture 250 of attribute emphasizing images of an identical tomographic plane, and FIG. 10B, a picture 260 of images of an identical tomographic plane scanned at different times.

The attribute emphasizing picture 250 presents standard images 251, 252 with attribute(s) emphasized in different manners. The emphasis of attribute can be set at the condition setting section 221 in a format corresponding to a content of the attribute, such as for utilization of different kinds of windows, processes by different functions, layout of differential images, enlargement, zooming, etc. Viewpoint is thereby focused, and contrast is increased with different average levels or light and shade tones, permitting even a catch of faint changes such as of small vessels or light contrast.

The time-differential picture 260 presents a current standard image 261 of a certain tomographic plane, and an image 262 of the plane processed relative to a different temporal point, thereby allowing one to know e.g. the degree of a change up to a current time with respect to CT values of regions of interest to be monitored. Heartbeats or breathing can be grasped to thereby permit a CT data monitoring at an effective phase.

Figure 11A:
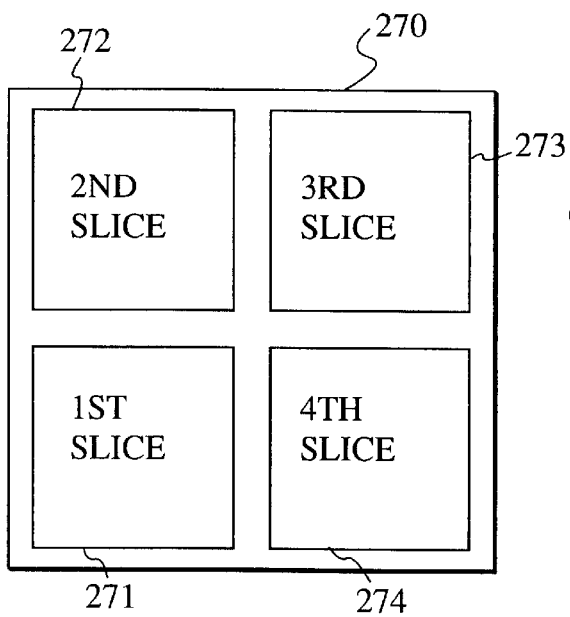
Figure 11B:
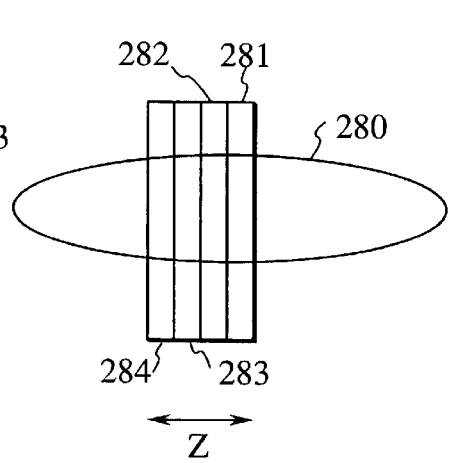

FIG. 11A illustrates a plurality of exemplary slice images 271–274 to be displayed on the monitor 13a in a multiple slice mode, and FIG. 11B, scanned portions 281–284 presented by slice positions (detectors) in correspondence to the images 271–274 in a longitudinal direction Z of a patient 280.

The image processing device 200 is adapted for execution of a combination of the image processing techniques described.

One or more regions of interest can be set in each tomographic image displayed on the monitor 13a. As such, in the multiple slice system in which different slice planes are substantially concurrently acquired, respective slice planes may have their ROI's set thereon under associated circumstances, where blood vessels' running state may be inadequate for the setting, e.g. such that different blood vessels may either be blocked and the other be running well on a first slice plane, and concurrently the former may be running well on a second plane while the latter may be blocked on this plane. Even in such a case, the embodiment allows for a plurality of tomographic images different in slice position to be displayed, thus permitting the trigger timing to have an increased accuracy.

In the foregoing embodiments, a region of interest is set to a relatively large blood vessel, and a quantity of contrast medium is let through the blood vessel to perform a continuous monitoring of an average CT value. Under this condition, if the patient be a phantom, it would not move, so the region of interest would be kept in position. The patient however is a human body, and in this case, it may show its living actions, such as a cough or sneeze for example, thereby causing a scan position to be deviated from a set position.

How the CT value varies when the scan position is deviated depends on what is present where it is deviated. Even where a similar organ exists relative to before deviation, unless a sufficient quantity of contrast medium arrives there, the average CT value will not reach a threshold value even after a lapse of time, and no automatic start of a second scan takes place. In this case, a visual check is made for a presence or absence of contrast medium on a screen, and a second scan is started at a discretion of an operator.

In a region after deviation, there may be an organ, such as a bone for example, that may provide raised CT values, and in this case, the average CT value will exceed a threshold value upon an occurrence of the deviation, causing a second scan to start at an inadequate timing.

To this point, one can set a smaller region of interest to be kept from jutting out of a desirable region even if it is somewhat deviated, but there is not given an essential solution, and besides, the average CT value gets more susceptive to the influence of noises.

Alternatively, one may always monitor movements of a patient and correct coordinates of a region of interest defined in a coordinate system of the examination system in dependence on a variation of a coordinate system of the patient, which correction however needs a remarkable quantity of computer resources, if it is to be executed in real time, in addition to an apprehension such that coordinate corrections in a longitudinal direction of the patient renders difficult the analysis of a CT image in a second scan, failing to keep a sufficient clinical applicability.

Figure 12:
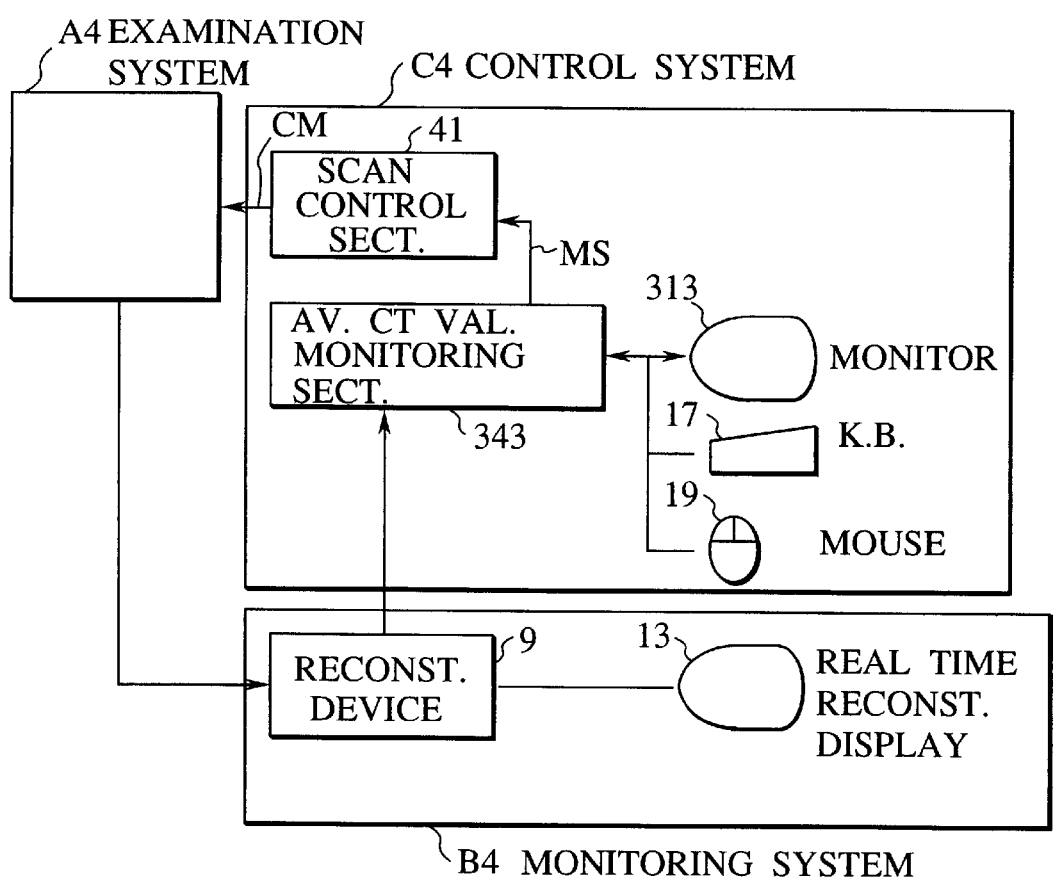
FIG. 12 is a block diagram of an X-ray CT apparatus according to a fourth embodiment of the invention.

With such points in view, there will be described an X-ray CT apparatus CT4 according to a fourth embodiment of the invention, with reference to FIGS. 12 to 16. FIG. 12 shows the X-ray CT apparatus CT4 in a block diagram.

The X-ray CT apparatus CT4 according to the fourth embodiment comprises an examination system A4, a monitoring system B4 and a control system C4 each having like functions to the embodiments described, and has constitution and functions additionally described hereunder.

In the X-ray CT apparatus CT4 the control system C4 has a scan control section 41, and an average CT value monitoring section 343 provided with input/output interfaces such as a ROI setting monitor 313. It is noted that the ROI setting monitor 313 may have an identical screen or identical pictures to a real time reconstruction image display 13 of the monitoring system B4, and that the average CT value monitoring section 343 may be included in the monitoring system B4, although the section 343 has a region-of-interest setting function, a monitoring condition setting function and a decision function, and it is shown as a component of the control system C4.

The X-ray CT apparatus CT4 is constituted such that a patient is detected for a movement thereof to thereby temporarily stop a starting of a second scan based on a CT value monitoring.

More specifically, when a position and a configuration of a region of interest (hereafter called "normal ROI") are set in a described manner for a real-time CT value monitoring system, an additional region of interest (hereafter called "stop ROI") is separately set, As a position for the stop ROI, there is selected a location, such as on a back born for example, which little varies or whose average CT value is substantially kept unchanged even when a time has elapsed, unless the patient moves in a given tomographic image. It is now assumed that "normal ROI=single" and "stop ROI= single".

Upon a setting of the respective regions of interest, their monitoring conditions are set at the average CT value monitoring section 343. The monitoring conditions include a threshold value for an average CT value of the normal ROI, and a CT value condition for specifying a permissible variation width of an average CT value of the stop ROI.

The average CT value monitoring section 343 provides a monitor signal MS for informing the scan control section 41 of a variety of monitoring results. The monitor signal MS is controlled to have, when the average CT value of the normal ROI exceeds the threshold value therefor, a signal state permitting a start command of the second scan to be output, and while the average CT value of the stop ROI is deviating from the specified width therefor, a signal state which does not permit the start command to be output.

Thereby, such an event is possibly prevented that an unexpected action of the patient causes a second scan to start at an inadequate timing.

There will be described functions of the control system C4, with reference to FIGS. 13A, 13B, 14A, 14B, 15A, 15B and 16, in which FIGS. 13A, 13B, 14A, 14B, 15A and 15B illustrate exemplary presentations on a screen 131a. For convenient description, the screen 313a is assumed as a screen of the monitor 313, and it may be a screen of the real time reconstruction display 13.

Figures 13A, 13B:
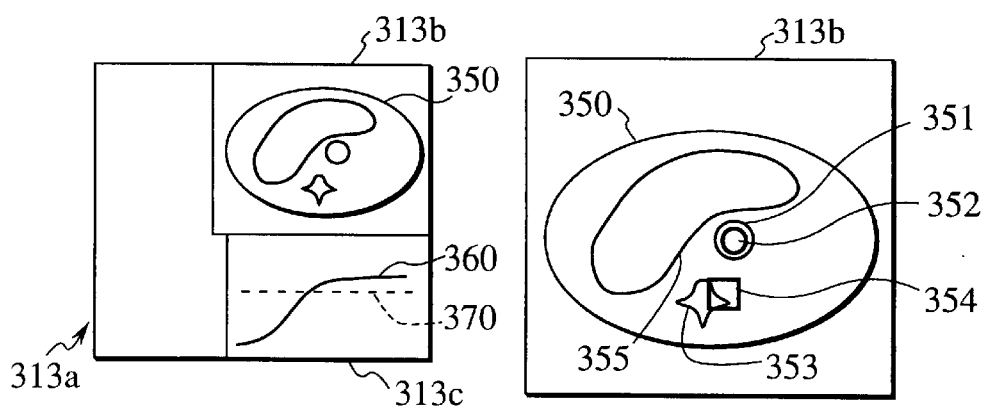

As illustrated in FIG. 13A, there are displayed on the screen 313a a reference image window 313b and a CT value monitoring window 313c.

In the reference image window 313b is displayed a CT image 350 based on a reference image acquiring scan, and in the CT value monitoring window 313c, an average CT value 360 of and a monitoring condition 370 for each ROI.

At first, at a step S41, a reference image 350 is acquired.

Next, at a step S42, as illustrated in FIG. 13B, there are set a normal ROI (as a region 352) and a stop ROI (as a region 354). The normal ROI is set, e.g. as a circular region 352 of interest, at a location vicinal to an organ 355 as an object to be examined and easy to grasp a movement of contrast medium, e.g. on a blood vessel 351 constituting a big arterial blood vessel. The stop ROI is set, e.g. as a rectangular region 354 of interest, at a location having a tendency to provide a remarkably changed average CT value upon deviation of position, e.g. at part of a back bone 353 including a boundary with another organ.

Figure 14A:
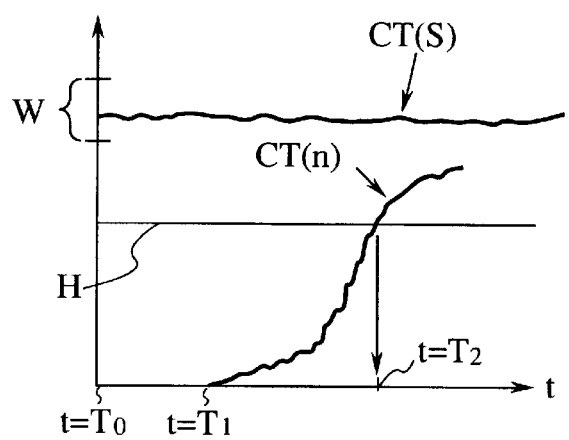

When the regions of interest are set, associated monitoring conditions are set, as necessary, and a monitoring of average CT value is started at t=T0. As illustrated in FIG. 14A, the monitoring conditions include a threshold value H for an average CT value CT(n) of the normal ROI, a specified width W for an average CT value CT(s) of the stop ROI.

Thereafter, contrast medium is injected, and a completion of injection is informed.

Then, at a step S43, the first scan starts for a monitoring.

At a step S44, the average CT values CT(n), CT(s) of the normal and stop ROIs are calculated.

At a step S45, a decision is made of whether or not an elapsed time (t−T1) along the first scan is within a set limit of time interval, and if the time limit is exceeded (NO), the flow goes to a step S46 to stop the first scan. When the elapsed time is within the time limit, the flow goes to a step S47.

Figure 15A:
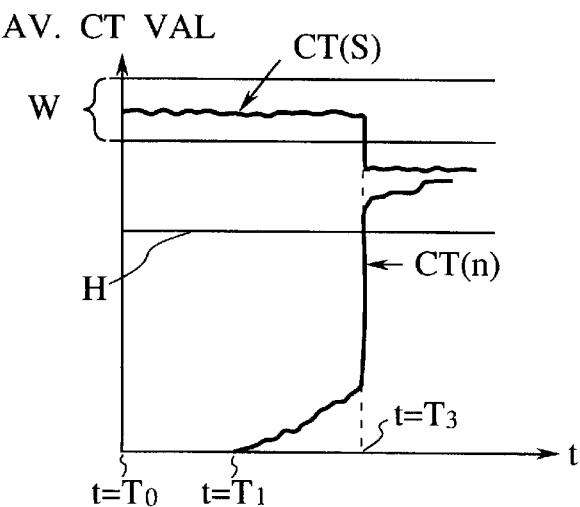

At the step S47, a decision is made of whether the average CT value CT(n) of the normal ROI is in excess of the threshold value H, as it is raised due such as to an arrival of contrast medium or for other reason, as illustrated in FIG. 14A or 15A. If the average CT value CT(n) is in excess of the threshold value H (YES), the flow goes to a step S48. Incidentally, in FIG. 15A, the average CT value CT(n) of the normal ROI is in excess of the threshold value H, as the patient has suddenly (at t=T3) moved sideways, causing the set position 352 of the normal ROI to deviate from the blood vessel 351, jutting into a peripheral region relatively high of CT value.

At the step S47, unless the average CT value CT(n) is in excess of the threshold value H (NO), the flow goes to the step S44, where average CT values CT(n), CT(s) are again calculated in a subsequent clock frame. In other words, the first scan is continued.

Figure 14B:
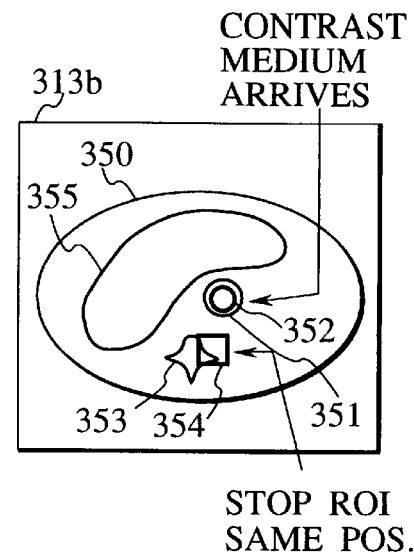

At the step S48, a decision is made of whether the average CT value CT(s) of the stop ROI is kept within a range of the specified width W. When an arrival of a dense flow of contrast medium has begun (t=T2), if the set region 354 of the stop ROI is lying on a substantially identical location to the part of the back bone 353 as an initial object of setting, as illustrated in FIG. 14B, then the average CT value CT(s) of the stop ROI is kept within the range of the specified width W (YES), as illustrated in FIG. 14A, and the flow goes to a step S49, where a start of the second scan is permitted substantially at the point t=T2.

Figure 15B:
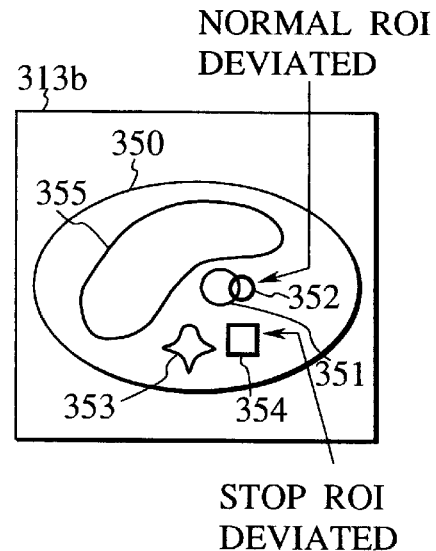

However, as illustrated in FIG. 15B, if the set position 354 of the stop ROI is caused to deviate from the back bone 353, moving toward a peripheral region relatively low of CT value, then as illustrated in FIG. 15A, the average CT value CT(s) of the stop ROI deviates out of the specified width W, i.e. absent from the range of the specified width W (NO), and the flow goes to the S44 for continuation of the first scan. In other words, the flow is kept from going to the step S49, and the second scan is not permitted to start.

There may be employed a single stop ROI and a plurality of normal ROI's.

Figure 16:
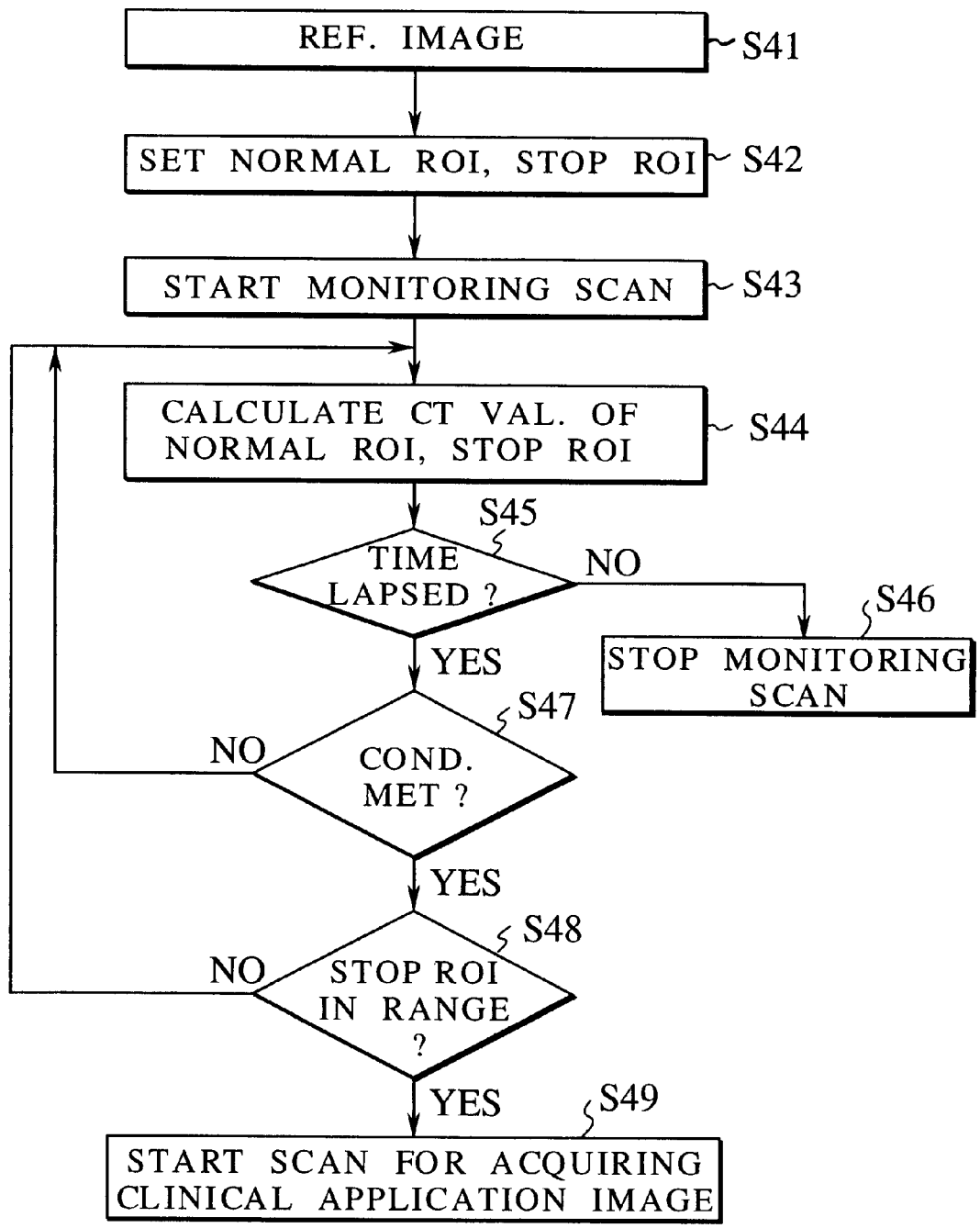
FIG. 16 is a flowchart describing a manual mode.

For this case, one may employ a control system in which one normal ROI as well as the stop ROI is monitored by the control flow of FIG. 16, the remaining normal ROI's are assumed to be a plurality of regions of interest in the first embodiment and monitored by the control flow of FIG. 4, and the affirmative (YES) flow at the step S48 of FIG. 16 interrupts between the steps S31 and S33 in the control flow of FIG. 4.

As will be seen from the foregoing description, according to the invention, as an adequate number of regions of interest are set in a first scan, and a monitoring of respective CT values are performed with a necessary accuracy, they are selectively employable individually of the regions of interest or in combination between the regions of interest to thereby provide a competent or better base of decision to or than always grasping a CT value of a single region of interest at a high accuracy, permitting a second scan to be executed at an adequate timing.

For example, eve when a real time disturbance is caused such as by a movement of a patient, its influences can be detoured or canceled, or coped with by a weighting process or correction or change of conditions for a decision.

The allotment of computer resources for setting a plurality of regions of interest is kept within an increase of an arithmetic series, as well.

Further, a complementary use of regions of interest is allowed, permitting an increased flexibility in selection of position.

Further, as the region of interest to be monitored can be set to be plural in number, a resultant allowance for application permits a variety of additional services.

While preferred embodiments of the present invention have been described using specific terms, such description is for illustrative purposes, and it is to be understood that changes and variations may be made without departing from the spirit or scope of the following claims.

What is claimed is:

1. An X-ray CT apparatus adapted to perform a monitoring of a CT value of a region of interest by a first scan and, when the CT value meets a predetermined condition, to execute a second scan for acquiring a clinical application image, wherein the X-ray CT apparatus has region-of-interest setting means adapted for setting a plurality of regions of interest for the monitoring to be performed.

2. The X-ray CT apparatus of claim 1, further comprising:
condition setting means adapted relative to regions of interest set by the region-of-interest setting means, for setting as the predetermined condition CT value conditions to be met by individual CT values of the regions of interest;

decision means for deciding whether the CT value conditions are all met at corresponding regions of interest to provide a result of decision; and control means responsible for the result of decision to start the second scan.

3. The X-ray CT apparatus of claim 1, further comprising:
condition setting means adapted relative to regions of interest set by the region-of-interest setting means, for setting as the predetermined condition CT value conditions to be met by individual CT values of the regions of interest and a condition for defining a decisive operation between the regions of interest;

decision means for deciding whether the CT value conditions are respectively met at corresponding regions of interest to provide individual results of decision of the regions of interest;

operation means employing the individual results of decision of the regions of interest for executing the decisive operation between the regions of interest to provide a result of operation; and control means responsible for the result of operation to start the second scan.

4. The X-ray CT apparatus of claim 1, further comprising:
condition setting means adapted, relative to regions of interest set by the region-of-interest setting means, for setting as the predetermined condition a CT value condition to be met by CT values between the regions of interest;

decision means for deciding whether the CT value condition is met between corresponding regions of interest to provide a result of decision; and control means responsible for the result of decision to start the second scan.

5. The X-ray CT apparatus of claim 1, further comprising:
decision means for deciding whether the CT value of a region of interest set by the region-of-interest setting means meets the predetermined condition;

monitoring means for monitoring a change of the CT value of another region of interest set by the region-of-interest setting means; and control means responsible for a result of monitoring of the monitoring means to stop a start of the second scan.

6. The X-ray CT apparatus of claim 1, further comprising:
memory means for storing therein information on relationships between the predetermined condition and positions of regions of interest the region-of-interest setting means can set; and display means for displaying a list of information stored in the memory means.

7. The X-ray CT apparatus of claim 1, further comprising display means for concurrently displaying a plurality of CT images in which regions of interest can be set by the region-of-interest setting means.

8. The X-ray CT apparatus of claim 7, wherein the plurality of CT images comprise CT images of an identical tomographic plane acquired at different times.

9. The X-ray CT apparatus of claim 7, wherein the plurality of CT images include CT images emphasizing different attributes of an identical tomographic plane.

10. The X-ray CT apparatus of claim 7, wherein the plurality of CT images include CT images presenting different tomographic planes.

* * * * *